United States Patent [19]
Pannell et al.

[11] Patent Number: 5,426,037
[45] Date of Patent: Jun. 20, 1995

[54] PRODUCTION OF MONOCLONAL ANTIBODIES

[75] Inventors: Richard Pannell, Suffolk; Cesar Milstein, Cambridge, both of England

[73] Assignee: Medical Research Council, London, England

[21] Appl. No.: 167,801
[22] PCT Filed: Jun. 1, 1992
[86] PCT No.: PCT/GB92/00982
§ 371 Date: Dec. 14, 1993
§ 102(e) Date: Dec. 14, 1993
[87] PCT Pub. No.: WO92/22634
PCT Pub. Date: Dec. 23, 1992

[30] Foreign Application Priority Data

Jun. 14, 1991 [GB] United Kingdom .................. 9112836

[51] Int. Cl.⁶ ...................... C12M 3/00; C12M 1/28; C12N 5/08; C12P 21/08
[52] U.S. Cl. .................. 435/70.21; 435/240.22; 435/240.25; 435/240.27; 435/286; 435/296; 435/312; 435/315; 435/316
[58] Field of Search .............. 435/284, 286, 287, 294, 435/312, 313, 314, 315, 316, 240.2, 240.25, 240.26, 240.27, 240.3, 240.31, 40.21, 240.22, 296

[56] References Cited

FOREIGN PATENT DOCUMENTS 2934328 3/1981 Germany .
3900020 7/1990 Germany .

*Primary Examiner*—William H. Beisner
*Assistant Examiner*—Nancy J. Degen
*Attorney, Agent, or Firm*—Lee, Mann, Smith, McWilliams, Sweeney & Ohlson

[57] ABSTRACT

Apparatus and method for the production of monoclonal antibodies, wherein a sealed dialysis tube (18) is fixed within a roller bottle (10) to be immersed in a growth medium (24) contained within the roller bottle, the dialysis tube is filled with a culture of hybridomas (20) to the extent that a bubble (22) remains within the tube, and the bottle is rotated or otherwise moved in order to cause the bubble to oscillate back and forth from one end of the tube to the other.

14 Claims, 2 Drawing Sheets

PRODUCTION OF MONOCLONAL ANTIBODIES

FIELD OF THE INVENTION

This invention relates to a method of and apparatus for the production of monoclonal antibodies (MAbs).

BACKGROUND TO THE INVENTION

MAbs are typically prepared by in vivo cultivation of hybridomas in the peritoneal cavity of mice as ascitic rumours (Goding, 1980), which produces antibody concentrations of the order of 20 mg/ml. The simplicity, efficiency, and high concentration of the final product make ascitic fluid the preferred choice for laboratories requiring relatively small amounts of a large number of MAbs. There are ethical reasons to look for alternatives, but it would in any case be attractive to develop a simpler, and possibly cheaper, alternative tissue culture method capable of substituting ascitic fluid.

One known tissue culture method for MAb production involves growing hybridoma cultures to large volumes in roller bottles, and then concentrating the antibodies produced by use of ammonium sulphate precipitation. With this method, the cells can only be maintained healthily below $10^6$/ml. Another method involves concentrating the cells to $2 \times 10^6$ cells/ml or more in serumless medium for 3-4 days (Galfre and Milstein, 1981). This can improve the yield, and has added advantages in that the volume of the product is lower, and there are no foreign proteins present (eg. Foetal bovine proteins) to complicate purification. Moreover, these methods are cumbersome, take up valuable space in the incubator, and necessitate the use of large quantities of media, foetal calf serum (FCS), and ammonium sulphate.

Hollow fibre systems allow cells to be grown between narrow diameter hollow fibres, within a cartridge into which fresh medium is continuously pumped. Hybridomas can reach high densities, and production of MAbs is efficient (Schonherr and Gelder, 1988) However, the cost of such systems with associated software is high, and only justified when relatively large amounts of individual MAbs are required. This is also the case with fermenters and bioreactors. Growth of cells in dialysis bags within small culture bottles (Sjörgren-Jansson and Jeanson, 1990), although appropriate for laboratory use, is restricted to 25 ml per bottle.

THE INVENTION

According to one aspect of the present invention, there is provided a method of producing monoclonal antibodies according to which a dialysis tube immersed in a growth medium is filled with a culture of hybridomas to the extent necessary to leave a bubble in the tube and is sealed, and the bubble is caused to oscillate back and forth along the sealed dialysis tube in order to keep the culture of hybridomas in suspension.

In a preferred method, oscillation of the bubble is achieved by an oscillatory or rotary motion of the dialysis tube taking said tube continuously through two orientations, in one of which the bubble lies at one end the tube and in the second of which the bubble lies at the other end of the tube.

The required oscillatory or rotary motion of the dialysis tube can be achieved by fixing the tube within a container for the growth medium, and rocking or rotating the container. A preferred container is a roller bottle mounted with its longitudinal axis horizontal for oscillatory or preferably continuous rotation about a horizontal axis, the sealed dialysis tube being fixed within and between the respective ends of the bottle at positions angularly spaced around said longitudinal bottle axis, ie. so that the tube is skewed relative to said axis. The longitudinal axis of the bottle is preferably coincident with the axis of rotation.

Thus, according to another aspect of the invention, there is provided apparatus for the production of monoclonal antibodies, comprising a container for a growth medium, a dialysis tube fixed to and within the container so as to be immersed in the growth medium, and means for imparting such a motion to the container that, when the dialysis tube is filled with a culture of hybridomas to the extent necessary to leave a bubble in the tube and is sealed, the bubble will be caused to oscillate back and forth along said tube in order to keep the culture of hybridomas in suspension.

As mentioned above, a preferred container is a roller bottle mounted with its longitudinal axis horizontal and for continuous rotation about said axis, the dialysis tube being fixed within and between the ends of the bottle at positions regularly spaced around said longitudinal bottle axis, ie so that the tube is skewed relative to said axis.

A preferred arrangement has a plurality of, for example three, dialysis tubes fixed as aforesaid within the roller bottle.

For the or each dialysis tube, the roller bottle preferably has at one end a tube anchorage and at the other end an inoculation and sampling port which normally seals and anchors the tube but can be opened for filling and emptying the tube and sampling its contents (when the rotary motion of the bottle is stopped).

Additionally, at one end of the bottle, preferably the end opposite to the tube inoculation and sampling port or ports and preferably on the bottle axis, said bottle is provided with a port for filling and emptying the bottle with growth medium and for gassing said medium (again when the rotary motion of the bottle is stopped).

Preferably, either one or both the tube anchorage or anchorages and the tube inoculation and sampling port or ports are adjustable to enable the dialysis tube or tubes to be pulled taut between the ends of the bottle.

A preferred method of use of the apparatus comprises:

a) fixing a knotted end of dialysis tubing to an anchorage at one end of a roller bottle;

b) attaching the other end of the tubing to an inoculation and sampling port at the other end of the bottle, so that the tube is skewed within the bottle relative to the longitudinal axis of the bottle;

c) adjusting the anchorage to pull the skewed tube taut;

d) filling the tube with hybridoma culture to the extent necessary to leave a bubble inside the tube and then sealing the tube port;

e) substantially filling the bottle with a growth medium, gassing the growing medium and then closing the bottle filling and gassing port; and f) rolling the bottle about its longitudinal, horizontal axis.

A preferred hybridoma culture is in the pre-stationary phase, typically having between 4 and $8 \times 10^5$ cells/ml. A preferred growth medium is Dulbecco's Modified Eagle Medium (DMEM), without serum, and a preferred gassing medium is a $CO_2$/air mixture, conveniently 5% $CO_2$ to 95% air. A preferred rate of rotation of the bottle is about 1.5 revs/min.

BRIEF DESCRIPTION OF THE DRAWINGS

The method and apparatus in accordance with the invention are exemplified in the following description, making reference to the accompanying drawings, in which.

THE APPARATUS

Figure 1:
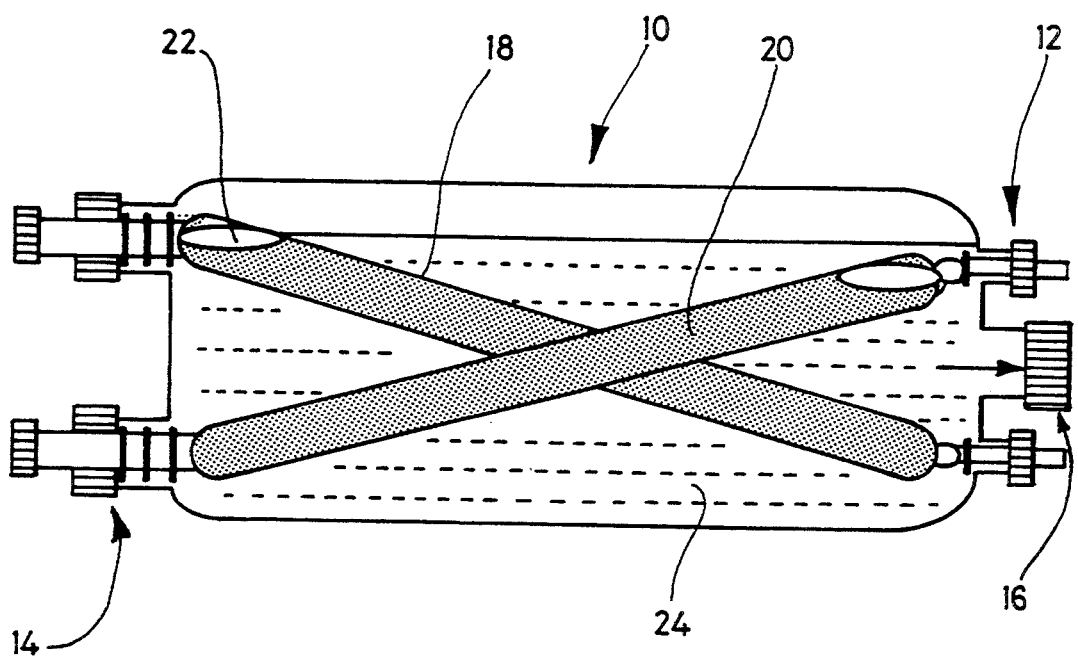
FIG. 1 shows a roller bottle with dialysis tubes mounted therein, as prepared ready for use.

Referring first to FIG. 1, the production, form and preparation of the apparatus will first be described.

A boro-silicate glass roller bottle 10, approximately 2 litres in volume, is constructed as shown in the drawing, with three angularly spaced tube anchorages 12 at one end and three tube filling, emptying and sampling ports 14, correspondingly angularly spaced at the other end. A bottle filling, emptying and gassing port 16 is provided on the axis of the bottle at one end thereof.

The tube anchorages 12 comprise solid inserts incorporating means of displaceable adjustment in the longitudinal direction of the bottle, whilst the tube ports 14 comprise hollow glass inserts O-rings and cap seals. Again, these hollow inserts incorporate means of displaceable adjustment in the longitudinal direction of the bottle.

Dialysis tubing 18 was obtained from Medicell, London, with a flat width of 3.2 cm (Visking—approx cut off 10,000 Daltons). It was heated to 80° C. in sodium bicarbonate/EDTA buffer for 30 mm, then stored in EDTA/azide at 4° C. It was washed thoroughly with distilled water prior to use in the culture vessel.

The preparation of the apparatus involves fastening the knotted end of the pre-washed tubing to the anchors, and threading the other end through the ports, setting the tubing 18 on the skew relative to the bottle axis, as shown. The tubing is fastened to the glass inserts by use of the O-rings, the cap-seals are tightened, and the tubing is pulled taut by using the adjustment at the port and anchorage ends. The tubing and the bottle are then filled with distilled water and autoclaved.

After sterilisation, the water is poured out, cell cultures 20 are placed inside the tubing 18, leaving a bubble 22 in each tube, via the inoculation ports 14, and 1.5 litres of DMEM without serum, referenced 24, is put in via the bottle port 16 at the anchorage end. The medium is then gassed with 5% $CO_2$/95% air. All ports are then sealed.

Conditions were varied when experimenting with the system with respect to cell concentration, and the percentages of FCS added inside and outside the tube. The results given herein reflect the most straightforward and efficient methods.

CULTURE CONDITIONS 30 ml hybridoma cultures pre-stationary phase, typically at between 4 and $8 \times 10^5$ cells/ml, were transferred to the bubble chambers and DMEM +5% FCS was added until the tubing was nearly full (average final density approx. $2 \times 10^5$ cells/ml). 1.5 litres of DMEM in the absence of serum was added to the main body of the roller and gassed using a mixture of 5% $CO_2$/95% air. The apparatus was then rolled at 1.5 revs per min. The medium was gassed daily and replaced at day 3, after which it was changed on alternate days. This schedule is not necessarily either optimal or simplest. The cultures were allowed to carry on until the cells had died out (14–20 days). For speedier results, the cells were concentrated by centrifugation to $1-2 \times 10^6$/ml before introduction into the roller, after growth in a 75 cm flask.

QUANTITATION OF ANTIBODY CONCENTRATION

Falcon 3912 Flexiplates were coated with a RaMIg (Dako Z259). The sups were titrated onto this, the degree of binding being detected by RaMIg-HRP (Dako P260) followed by the peroxidase substrate, ABTS [2,2'-azinobis (3-ethylbenzthiazolinone sulfonic acid)]. Purified Ig from the appropriate hybridoma of known concentration was titrated at the same time, and a standard curve was constructed. The OD readings of the sups were interpolated from the standard and multiplied according to their dilution (see FIG. 2). Rat MAb 187.1 was detected by a similar method, using MRCOX12. Some samples were purified by protein A column chromatography, and the yield of purified antibody determined by spectrophotometry.

Figure 2:
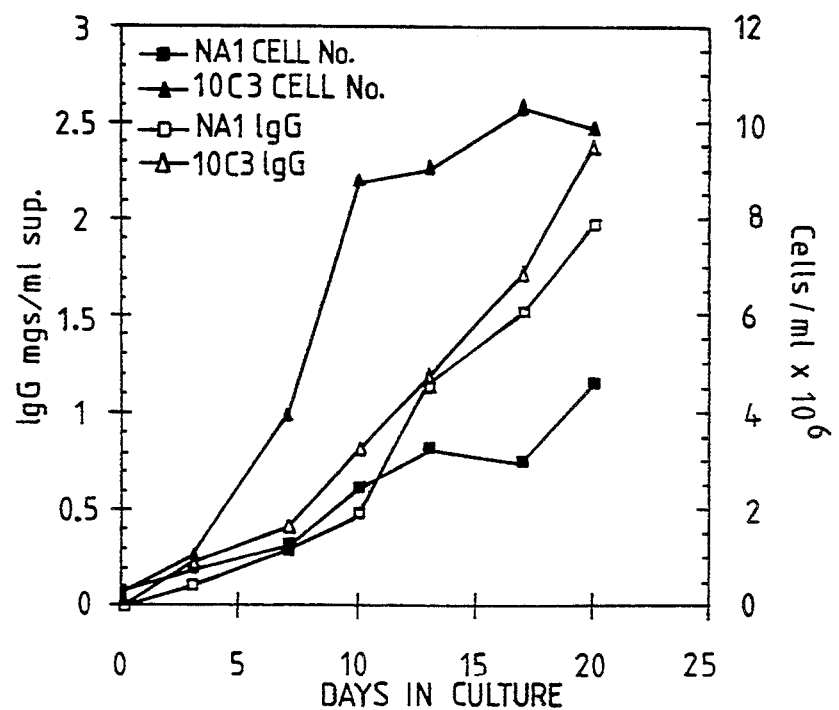
FIG. 2 is a diagram to show the results of quantitation of antibody concentrations obtained by use of the apparatus of FIG. 1.

FIG. 2 details cell growth (full symbols) and IgG production (open symbols) obtained by use of the apparatus of FIG. 1. The figure shows that growth and IgG production can vary between cell lines.

RESULTS

Cells typically grew to between $4 \times 10$ and $10^7$/m, the viability dropping off around 7 days to reach a plateau of 10–20% for several days before eventual death (20–25 days). It is possible that cell viability could be improved by gassing with an oxygen/$CO_2$ mix when the cells become concentrated (Sjorgren-Jansson and Jeanson, 1985). The cells within the tubes in the apparatus were gently stirred, due to the skew orientation of the tubes, the rolling motion causing the air bubble inside the tube to oscillate, which was seen to be highly advantageous for maintaining the cells in suspension. After a variable induction period, there was an initial period of fast growth, and although the doubling time was slower than in a standard culture, the cell density was much higher. The ratio of cell number to antibody production varied considerably with different cell lines. For example, NA1 only reached a cell density of $3.7 \times 10^6$/ml, and yet produced almost as much MAb as 10C3, on the other hand, which attained a density of $1.03 \times 10^7$ cells/ml (see FIG. 2).

We usually include 5% FCS, inside the dialysis compartment. The serum impurities in the sample are effectively lower when compared with ascitic fluid. Serum-free preparations were tried and also gave reasonable titres; i.e. DMEM minus serum and DCCM2 serum-free medium from Biological Industries (see appended Table 1).

Antibody concentration increased up to 18–20 days, without too much degradation of the dead cells. Results indicate that some antibody production may continue after apparent total cell death, (see FIG. 2—no plateau of Ig production) but as the cells begin to disintegrate, the contamination by intracellular proteins increases. It is therefore preferred to stop cultures at this stage, at the expense of larger MAb concentration.

To make a comparison of active MAb obtained in bubble chambers and ascitic fluid the binding activity of anti-oxazolone MAb, NQ10 was measured by a conventional ELISA method. The result (Table 2) shows that while the IgG content was 7 times lower, the activity is only 1.5 fold less in bubble chamber supernatant compared to ascites. In addition two hybridomas which produce MAbs against cell surface proteins (CD1$a$ and CD1$c$) were grown in the oscillating bubble chambers. The binding of these antibodies to the cell surface of transfectants expressing individual CD1 epitopes was measured using a Becton & Dickinson FACScan apparatus. Maximum binding was obtained at dilutions of 1/500 to 1/1000. The average increase in IgG binding over normal spent sup. was between 10 and 15-fold, and only a factor of 2-3 less than with the ascites which have been prepared, as will be clear from FIG. 3, which shows the production of MAbs against human cell differentiation antigens, bound antibody to cells being measured by indirect immunofluorescence (Bilsland 1989).

GENERAL

Procedures for the preparation of MAbs in dialysis tubes have been previously published. In one example, (Sjorgren-Jansson and Jeanson, 1985 and 1990), dialysis tubes are placed inside a flask, allowing small volumes to be grown and non-uniform mixing of cells within the membranes. Haard et al. (1988) propose dialysis tubing within roller bottles, which increases the volume of cultures within the membranes, but does not ensure that the cells grow in homogeneous suspension. In accordance with the present invention, the suspension problem is solved by means of an oscillating bubble. At the same time, a roller apparatus is proposed which is simple to use, and easily adaptable to daily laboratory routine. Glass bubble-chamber rollers are re-usable, and relatively inexpensive to manufacture. With the three-port vessel above described, each port can hold a different hybridoma, but a vessel with more or less ports could be made with ease. A larger number of ports would probably require more frequent changing and gassing of the medium. Currently a slightly longer roller vessel is being produced, where the volume of culture inside each tube will be 100 ml. The design is sufficiently simple to be considered manufacturable in sterile plastic.

Figure 3A:
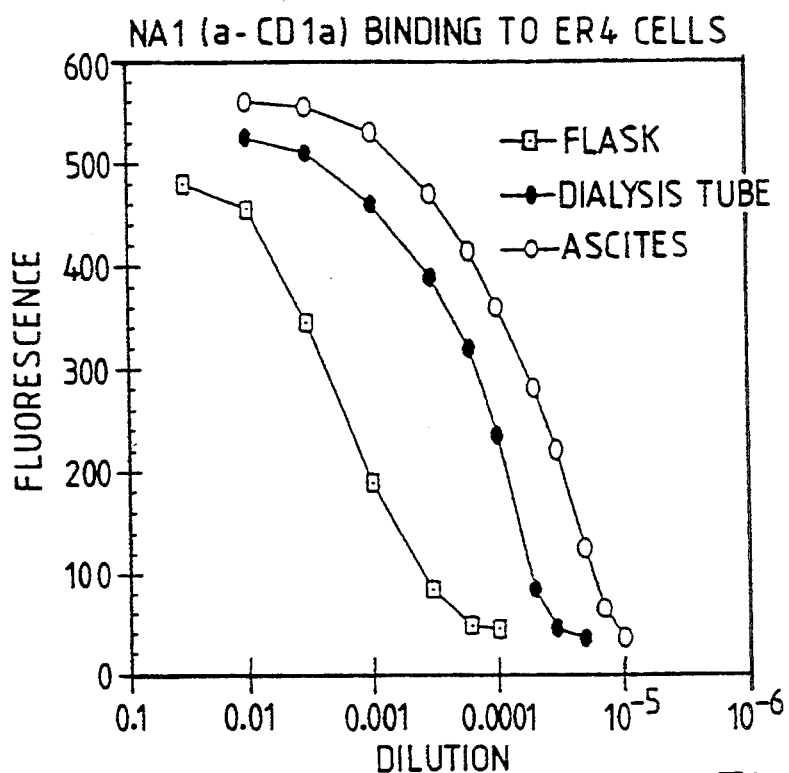
FIG. 3A and 3B are diagrams showing comparisons of the results of binding to ER4 cells and NR7 cells for different methods of production of monoclonal antibodies.
Figure 3B:
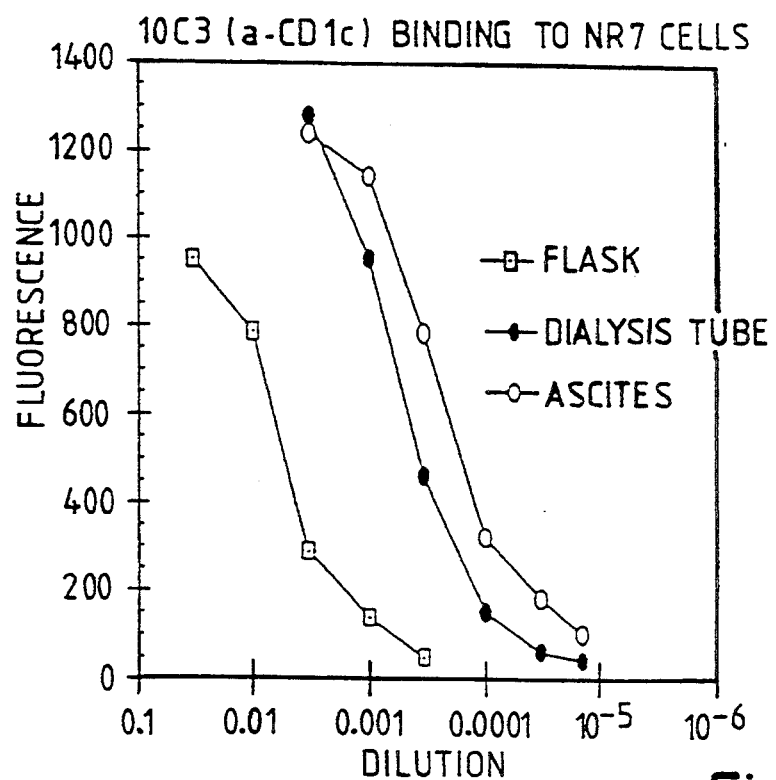

Semi-continuous culture of cell lines is made possible by allowing cells to settle when the viability is not too low, and removing most of the supernatant and debris. Alternatively, at the end of a batch, after the cells and sups have been removed, a new culture of the same cell line can be introduced after flushing out the debris. The IgG concentration obtained about 1/10 of that in ascitic fluid but contains only 5% FCS. Furthermore the comparisons of FIG. 3 show that as far as active antibody is concerned, the concentration of ascitic fluid is enriched only three-fold over the supernatants prepared in the oscillating bubble chamber of this invention. Another MAb (anti-oxazalone NQ10) also gave better enrichment when measured by its binding activity rather than its IgG content. Thus, the ratio of active MAb to FCS is better or considerably better in the bubble chamber supernatant, than the ratio of active MAb to mouse serum in the ascitic fluid. This advantage is further enhanced by the lower concentration of critical proteins (eg. immunoglobulins) present in FCS relative to mouse serum.

With the aid of media supplements and serum-free media, conditions can quite easily be optimised to produce even more pure MAbs for laboratories who require them. The above described apparatus produced abundant quantities of MAbs for most laboratory needs. More antibody is produced within each bubble chamber than in one mouse, with little effort, and without the need for animals.

In conclusion, in order to practise the invention, a simple roller bottle has been constructed to house three dialysis tubes, each with a capacity of 75 ml. Cells are grown inside the dialysis tubing, which is immersed in ordinary DMEM medium without serum supplement. Cultures of hybridomas at medium or low density ($2 \times 10^5$ cells/ml) can be expanded directly in the dialysis tubes and attain a high cell density in the order of $10^7$/ml. Continuous gentle stirring of the cells is obtained, as the design causes a bubble to oscillate along the length of each tube. The six cell-lines tested all gave antibody concentrations of between 1.1 and 2.3 mg/ml at 20 days. Such an in vitro apparatus obviates the need to employ ascites production, because it is as simple or simpler than the injection of mice, and the in vitro product is very rich in antibody, whilst containing low amounts of contaminating proteins. With this apparatus, it has proved possible to prepare up to 0.5 g of MAb in 20 days, within a single rolling bottle, starting with a 30 ml culture taken from an ordinary 25 cm² flat-bottomed flask.

Various modifications to the above-described arrangement are possible within the scope of the invention hereinbefore defined, for example to facilitate laboratory use. For instance, the bottle could be manufactured in plastics instead of glass, and be disposable. One possibility is to make the whole bottle in plastics with dry dialysis tubes in position and then to sterilise.

An alternative would be to have re-usable glass (or plastic) bottles, and to insert disposable dialysis membranes. These tubes could be supplied already mounted, and kept extended by suitable obvious devices. The tubing used in the present apparatus is Visking, but other suitable substitutes are obvious alternatives, especially if better suited to a rigid structure.

| | IgG PRODUCTION IN BUBBLE CHAMBER CULTURES | | | | |
|---|---|---|---|---|---|
| Cell-line | Maximum Cell no. × 10⁶/ml | Days in culture | Ig Concn mg/ml (ELISA) | Recovered as Pure Ig mg/ml. sup. | Flask culture mg/ml sup. |
| Na1/34 | 3.7 | 18 | 2.44 | 0.95 | 0.182 |
| WM25 | 7.1 | 18 | 1.34 | 0.47 | 0.137 |
| 10C3 | 10.3 | 20 | 2.13 | — | 0.192 |
| NQ10 | 4.8 | 11 | 1.81 | 0.55 | 0.077 |
| NQ10* | 1.8 | 7 | 0.84 | — | 0.077 |
| 9.E10 | 12.0 | 17 | 2.24 | 1.10 | 0.071 |

-continued

| IgG PRODUCTION IN BUBBLE CHAMBER CULTURES | | | | |
|---|---|---|---|---|
| Cell-line | Maximum Cell no. × $10^6$/ml | Days in culture | Ig Concn mg/ml (ELISA) | Recovered as Pure Ig mg/ml. sup. | Flask culture mg/ml sup. |
| 187.1 (rat) | 10.7 | 17 | 1.12 | 0.54*1 | 0.102 |

Most hybridomas are from mouse except 187.1 (rat) and were grown in 5% FCS/DMEM with no serum added to the outside medium. NQ10* was adapted and grown within the bubble chamber in serum-free medium, DCCM2 from Biological Industries (bathing medium contained 5% FCS).
*1 187.1 was purified using a DE52 column and a phosphate gradient.

TABLE 2
COMPARISON OF ANTIBODY TITRE AND IgG CONTENT

| MAb | Antigen | Antibody Titre Asc: Dial Sup. | IgG Content Asc: Dial Sup. |
|---|---|---|---|
| NA1 | CD1a | 2.7 | 7.3 |
| WM25 | CD1b | 4.7 | 10.5 |
| 10C3 | CD1c | 2.0 | 8.2 |
| NQ10 | Ox.bsa | 1.5 | 7.3 |

Antibody titres (i.e. the dilution which gives 50% maximal binding) were determined with the FACScan (as in FIG. 3) or by ELISA. The figures shown are the ratios between the titres of the materials shown.

REFERENCES

Adamson, S. R., Fitzpatrick, S. L., Behie, L. E., Gaucher, G. M. and Lesser, B. H. (1983) In vitro production of high titre monoclonal antibody by hybridoma cells in dialysis culture. Biotech. Letts. 5,573.

Berek, C., Griffiths, G. M. and Milstein, C. (1985) Molecular events during maturation of the immune response to oxazolone. Nature 316, 412.

Bilsland, C. A. G., Pannell, R., Gilmore, D. J. and Milstein (1989) Analysis of the CD1 panel on CD1 stable transfectants. In: Leucocyte Typing IV, (Ed. W. Knapp et al.), Oxford University Press, p. 260.

Evan, G. I., Lewis, G. K., Ramsay, G. and Bishop, J. M. (1985) Isolation of monoclonal antibodies specific for human c-myc proto-oncogene product Mol. Cell Biol. 5, 3610.

Favaloro, E. J., Bradstock, K. F., Kamath, S., Dowden, G., Gillis, D. and George, V. (1986) Characterisation of a p43 human thymocyte antigen. Disease Markers 4, 261.

Galfrè, G. and Milstein, C. (1981) Preparation of monoclonal antibodies. Methods in Enzymol. 73, 3.

Goding, J. W. (1980) Antibody production by hybridomas. J. Imm. Methods 39, 285.

Haardt, F. and Falkenberg, F. W. (1988) Alternative hybridoma culture procedure for the in vitro production of monoclonal antibodies. Proc. Miami Winter Symp. 8, 130.

Knazek, R. A., Gallino, P. M., Kohler, P. O. and Dedrich, R. L. (1972) Cell culture on artificial capillaries. Science 178, 65.

Köller, U., Groh, V., Majdic, O., Stockinger, H. and Knapp, W. (1986) Subclustering of CD1 antibodies on the basis of their reaction pattern with different types of dendritic cells. In Leucocyte Typing III (Ed. A. J. McMichael), Oxford University Press, p. 85.

McMichael, A. J., Pilch, J. R. Galfrè, G., Mason, D. Y., Fabre, J. W. and Milstein, C (1979). A human thymocyte antigen defined by a hybrid myeloma monoclonal antibody. Eur. J. Immunol. P, 205.

Rijner, A., van der Maaden, J., van Meel, F. and Olijve, W., (1987) An easy procedure for the production of serum-free monoclonal antibodies in dialysis tubing. Proc. 4th Eur. Congress on Biotech. Vol. 3, 609.

Schönherr, O. T. and van Gelder, P. T. J. A. (1988) Culture of animal cells in hollow fibre dialysis systems. An. Cell Biotech. 3, 337.

Sjörgren-Jansson, E. and Jeanson, S. (1985) Large scale production of monoclonal antibodies in dialysis tubing. J. Imm. Methods 84, 359.

Sjörgren-Jansson and Jeansson, S (1990) Growing hybridomas in dialysis tubing, optimisation of technique. Laboratory Methods in Immunology. 1, (Zola, E. Ed.) 41–50.

Yelton, D. E., Desaymard, C. and Scharff, M. D. (1981) Use of monoclonal anti-mouse immunoglobulin to detect mouse antivodies. Hybridoma 1,5.

We claim:

1. Apparatus for the production of monoclonal antibodies, comprising a container for a growth medium, a dialysis tube fixed to and within the container so as to be immersed in the growth medium, and means for imparting such a motion to the container that, when the dialysis tube is filled with a culture of hybridomas to the extent necessary to leave a bubble in the dialysis tube and is sealed, the bubble will be caused to oscillate back and forth along said dialysis tube in order to keep the culture of hybridomas in suspension.

2. Apparatus according to claim 1, in which the container is a roller bottle mounted with its longitudinal axis horizontal and for continuous rotation about said longitudinal axis, the dialysis tube being fixed within and between the ends of the roller bottle at positions angularly spaced around said longitudinal axis, so that the dialysis tube is skewed relative to said longitudinal axis.

3. Apparatus according to claim 2, having a plurality of dialysis tubes fixed as aforesaid within the roller bottle.

4. Apparatus according to claim 2 or claim 3, wherein, for each dialysis tube, the roller bottle has at one end a tube anchorage and at the other end an inoculation and sampling port which normally seals and anchors the dialysis tube but can be opened for filling and emptying the dialysis tube and sampling its contents when the continuous rotation of the roller bottle is stopped.

5. Apparatus according to claim 4, wherein, at the end of the roller bottle opposite to the tube inoculation and sampling ports, said roller bottle is provided with a port for filling and emptying the bottle with growth medium and for gassing said growth medium when the continuous rotation of the roller bottle is stopped.

6. Apparatus according to claim 5, wherein either one or both of the tube anchorages and the tube inoculation and sampling ports are adjustable to enable the dialysis tubes to be pulled taut between the ends of the roller bottle.

7. A method of producing monoclonal antibodies which comprises:
a) providing an apparatus according to claim 1;

b) filling the tube with a culture of hybridomas to the extent necessary to leave a bubble inside the tube and then sealing the tube;

c) filling the container with growth medium so that the sealed dialysis tube is immersed in the growth medium; and d) imparting a motion to the container such that the bubble is caused to oscillate back and forth along the sealed dialysis tube in order to keep the culture of hybridomas in suspension.

8. A method according to claim 7, wherein oscillation of the bubble is achieved by an oscillatory or rotary motion of the dialysis tube taking said dialysis tube continuously through two orientations, in one of which the bubble lies at one end of the dialysis tube and in the second of which the bubble lies at the other end of the tube.

9. A method according to claim 8, wherein the oscillatory or rotary motion of the dialysis tube is achieved by rocking or rotating the container.

10. A method according to claim 8, in which the container is mounted with its longitudinal axis horizontal for oscillatory rotation about a horizontal axis, and the sealed dialysis tube is fixed within and between the respective ends of the container at positions angularly spaced around said longitudinal axis, so that the dialysis tube is skewed relative to said longitudinal axis.

11. A method according to claim 10, wherein the longitudinal axis of the container is coincident with the axis of rotation.

12. A method of producing monoclonal antibodies which comprises:

a) fixing a knotted end of dialysis tubing to an anchorage at one end of a roller bottle;

b) attaching the other end of the dialysis tubing to an inoculation and sampling port at the other end of the roller bottle, so that the dialysis tubing is skewed within the roller bottle relative to the longitudinal axis of the roller bottle;

c) adjusting the anchorage to pull the skewed dialysis tubing taut;

d) filling the skewed dialysis tubing with hybridoma culture to the extent necessary to leave a bubble inside the tubing and then sealing the inoculation and sampling port;

e) substantially filling the roller bottle with a growth medium via a bottle filling and gassing port, gassing the growing medium via the bottle filling and gassing port and then closing the bottle filling and gassing port; and f) rolling the roller bottle about its longitudinal, horizontal axis.

13. A method according to claim 12, wherein the hybridoma culture is in a pre-stationary phase, having between 4 and $8 \times 10^5$ cells/ml, the growth medium in Dulbecco's Modified Eagle Medium (DMEM), without serum, and the growth medium is gassed with a gassing medium comprising a $CO_2$/air mixture.

14. A method according to claim 12, wherein the roller bottle is rolled at a rate of approximately 1.5 revs/min.

* * * * *